(12) United States Patent
Wuestenbecker

(10) Patent No.: US 9,488,604 B2
(45) Date of Patent: Nov. 8, 2016

(54) SYSTEM AND METHOD FOR THE AUTOMATED TESTING AND/OR MEASURING OF A PLURALITY OF SUBSTANTIALLY IDENTICAL COMPONENTS BY X-RADIATION

(71) Applicant: GE Sensing & Inspection Technologies, Hurth (DE)

(72) Inventor: Michael Wuestenbecker, Ahrensburg (DE)

(73) Assignee: GE Sensing & Inspection Technologies GMBH, Hurth (DE)

( * ) Notice: Subject to any disclaimer, the term of this patent is extended or adjusted under 35 U.S.C. 154(b) by 0 days.

(21) Appl. No.: 14/655,252

(22) PCT Filed: Dec. 18, 2013

(86) PCT No.: PCT/EP2013/077072
§ 371 (c)(1),
(2) Date: Jun. 24, 2015

(87) PCT Pub. No.: WO2014/102107
PCT Pub. Date: Jul. 3, 2014

(65) Prior Publication Data
US 2015/0330916 A1    Nov. 19, 2015

(30) Foreign Application Priority Data

Dec. 24, 2012    (EP) .................................... 12199331

(51) Int. Cl.
*G01N 23/04* (2006.01)
*G01N 23/18* (2006.01)
*G01N 1/00* (2006.01)

(52) U.S. Cl.
CPC .............. *G01N 23/046* (2013.01); *G01N 1/00* (2013.01); *G01N 23/18* (2013.01);

(Continued)

(58) Field of Classification Search
CPC ..................... G01N 23/046; G01N 2223/543; G01N 2223/645
See application file for complete search history.

(56) References Cited

U.S. PATENT DOCUMENTS

| | | | | | |
|---|---|---|---|---|---|
| 4,422,177 A | * | 12/1983 | Mastronardi | ........ | A61B 6/0457 378/10 |
| 4,872,187 A | * | 10/1989 | Nakahata | ............. | G01N 23/046 378/17 |
| 2002/0018542 A1 | * | 2/2002 | Fenkart | ................ | G01N 23/046 378/57 |
| 2011/0019796 A1 | * | 1/2011 | Wuestenbecker | .... | G01N 23/046 378/20 |

FOREIGN PATENT DOCUMENTS

| | | |
|---|---|---|
| DE | 20208174 U1 | 11/2002 |
| DE | 10260883 B3 | 7/2004 |

(Continued)

*Primary Examiner* — Robert Kim
*Assistant Examiner* — Eliza Osenbaugh-Stewar
(74) *Attorney, Agent, or Firm* — GE Global Patent Operation

(57) ABSTRACT

A system for the automated serial testing and/or measuring of a plurality of substantially identical components by X-radiation, the system comprising a testing device with a support, a rotor mounted so as to be continuously rotatable on the support, and an X-ray device disposed on the rotor, a protective enclosure surrounding the testing device, a handling device for handling a component during X-ray testing, and a control/evaluation unit configured for automatically controlling the system as well as evaluating the X-ray signals by computer tomography. The handling device is configured for periodically reciprocating between a loading region and a testing region and comprises an end face element on which the component can be disposed on the side of the end face.

20 Claims, 7 Drawing Sheets

(52) U.S. Cl.
CPC .............. *G01N 2001/002* (2013.01); *G01N 2223/1016* (2013.01); *G01N 2223/321* (2013.01); *G01N 2223/419* (2013.01); *G01N 2223/624* (2013.01); *G01N 2223/643* (2013.01); *G01N 2223/645* (2013.01)

(56) References Cited

FOREIGN PATENT DOCUMENTS

| | | |
|---|---|---|
| EP | 2253947 A2 | 11/2010 |
| EP | 2278305 A1 | 1/2011 |

\* cited by examiner

SYSTEM AND METHOD FOR THE AUTOMATED TESTING AND/OR MEASURING OF A PLURALITY OF SUBSTANTIALLY IDENTICAL COMPONENTS BY X-RADIATION

BACKGROUND

Embodiments of the invention relate to a system for the automated testing and/or measuring of a plurality of substantially identical components by X-radiation, comprising a testing device with a support, a rotor mounted so as to be continuously rotatable on the support, and an X-ray device disposed on the rotor, a protective enclosure surrounding the testing device, a handling device for handling the component during testing, and a control/evaluation unit configured for automatically controlling the system as well as evaluating the X-ray signals by computer tomography. Embodiments of the invention moreover relates to a method for operating such a system.

Systems of this type are used, for example, for the automated serial testing of castings, with the device being integrated into the production line of the manufacturer (inline testing).

One system of the type mentioned in the introduction is known, for example, from EP 2 278 305 A1. Components to be tested are pushed in a linear manner through the rotor by means of a belt conveyor extending through the testing device. The cross-sectional dimensions of the component to be tested are considerably limited due to a number of boundary conditions. First of all, the belt conveyor already takes up a part of the circular clear cross section of the testing device, which therefore is no longer available for the component itself. Secondly, the belt conveyor has to have a certain minimum width, so that due to the circular clear cross section, the belt conveyor cannot be disposed in the lowermost region of the clear cross section, whereby a considerable height is also lost. As a result, only a fraction of the actual clear cross section of the testing device is available for a component to be tested.

SUMMARY OF INVENTION

One of the objects of embodiments of the invention is to provide a CT system suitable for the inline testing of components and a corresponding method, which provide in the testing device a maximum clear cross section for the components to be tested.

According to an embodiment of the invention, the handling device is configured to execute a periodically reciprocating movement between a loading region and a testing region. It is thus a reciprocating handling device. In contrast to a conveyor passing through the testing device, the handling device according to an embodiment of the invention makes the entire clear cross section of the testing device available for the component because, according to an embodiment of the invention, the component can be accommodated at a universal end face element of the handling device, which is suitable for different accommodating/retaining means adaptable to the component. As a result, an embodiment of the invention enables the testing of components with a considerably larger cross-sectional surface area as compared to a conveyor passing through the testing device. Surprisingly, an embodiment of the invention does not entail any lengthening of the testing cycle because it was found that the testing device requires a certain cooling-off time after each testing process anyway, which can be used without any loss of time for unloading the tested component and loading the next component to be tested.

In an embodiment, the handling device is mounted on the side of the testing device or testing plane opposite to the loading region. This is advantageous in that the loading region can be free from structures for storing the handling device, so that the entire construction space in the loading region is available in particular for devices for loading and unloading components. In addition, the handling device can in an embodiment be disposed, substantially completely, inside the radiation protection enclosure, i.e. well-protected. Due to this feature, the handling device according to an embodiment of the invention differs, for example, from a conventional patient table for a medical CT system, where the patient mounts the table always on the side of the table base.

BRIEF DESCRIPTION OF THE DRAWINGS

The invention will be explained below with reference to embodiments and to the attached Figures. In the drawings.

DETAILED DESCRIPTION

Figure 1:
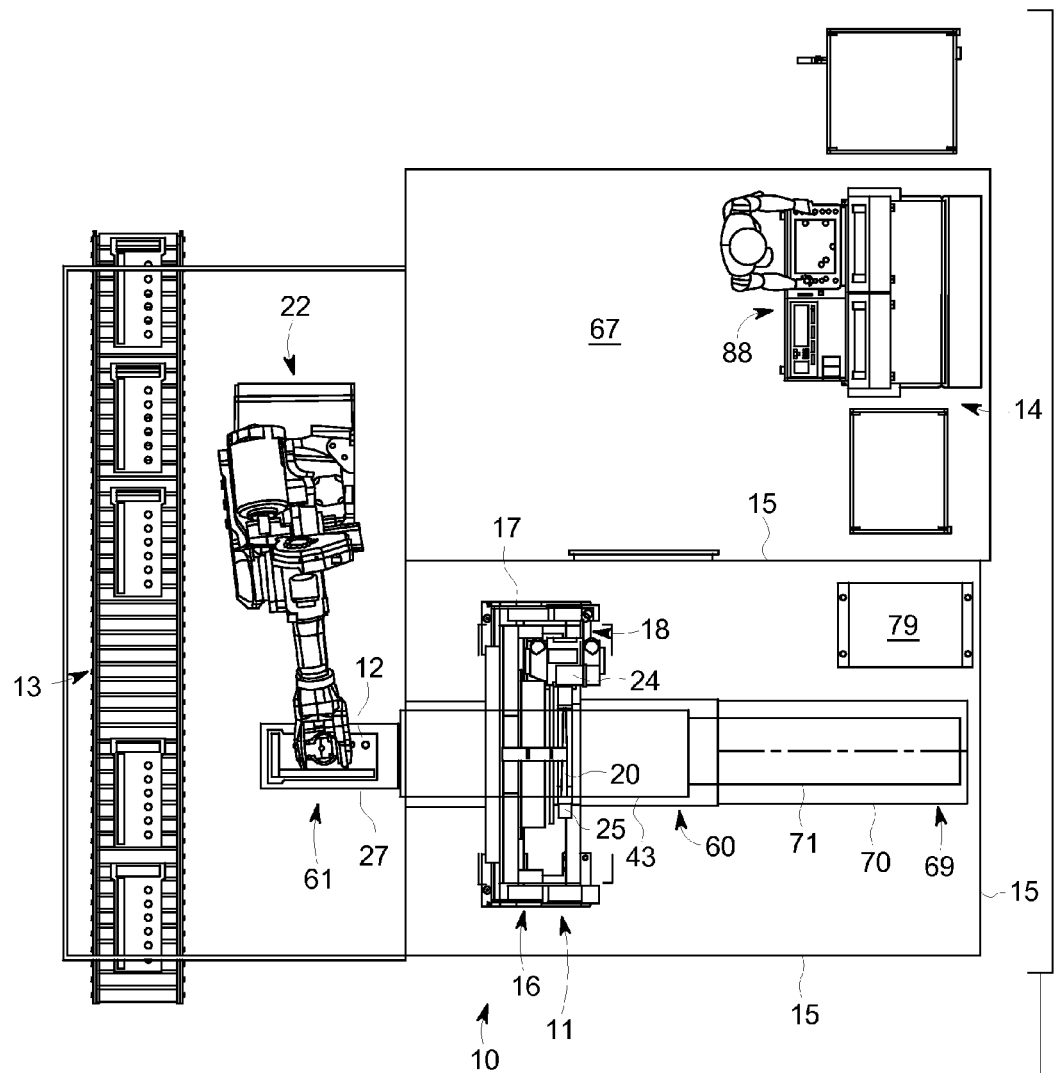
FIG. 1: shows a top view of a system for the serial X-ray testing of components in a production line.

The system 10 comprises a testing/measuring device 11, a handling device 60 for handling the component 12, particularly during X-ray testing in the testing/measuring device 11, an electronic control/evaluation unit 14 for controlling the system 10 and for evaluating the X-ray signals by computer tomography, and a protective enclosure 15 surrounding the testing/measuring device 11 for shielding the environment from the X-radiation generated by the Xray tube 24, in particular by means of a layer absorbing X-radiation, which contains lead, for example. A programmable or programmed control/evaluation unit 14 is typically disposed in an operating area 67 outside the radiation protection enclosure 15 and, for example, comprises an operating terminal 88.

The testing/measuring device 11 comprises a support 17, which is stationary during testing, and an annular rotor 18. The support 17 comprises a base frame 19 anchored to a ground plate 23. The annular part of the support 17 forms an annular rotation bearing for the rotor 18. The rotation bearing, the rotor 18 and the annular part of the support 17 form a ring unit 16 comprising a central ring opening 26 (see FIG. 7) for displacing a component 12 through the ring unit 16 during testing. In order to enable a horizontal orientation, the ring unit 16 is capable of being inclined, for example in a range of +−30° relative to the base frame 19, by means of a horizontal pivot bearing. The component 12 is, in an embodiment, conveyed through the rotor 18 axially parallel, i.e. parallel to the rotor axis.

An X-ray tube 24 and an X-ray detector 25 are attached opposite from each other on the rotor 18. The X-ray tube 24, which is, in an embodiment, configured as a rotary anode tube, is, in an embodiment, configured for generating a fan beam (20), see FIGS. 5 to 7. Alternatively, the X-ray tube 24 can be of the cone beam type. Expediently, the X-ray tube 24 is configured for illuminating the entire detector 25 with X-radiation 20 and for this purpose, in an embodiment, comprises a beam angle in one direction of at least 40°, in an embodiment at least 60°. In order to obtain a submillimeter resolution, the focus size of the X-ray beam is in an embodiment less than 1 mm, in an embodiment less than 0.7 mm. The tube 24 is in an embodiment operated with an energy of at least 80 kV, in an embodiment at least 100 kV, in an embodiment at least 120 kV, for example about 140 kV. With a view to a high penetration capability, higher X-ray energies of up to 450 kV are conceivable in an embodiment. In order to reduce the testing or measuring time, the X-ray tube 24 is in an embodiment operated with a continuous power output of at least 1 kW. In order to avoid problems due to excessive heat generation, the continuous power output is in an embodiment less than 10 kW. In an embodiment that is not shown, only the tube 24 may be attached to the rotor 18, while the stationary detector 25 forms a 360° ring.

Figure 5:
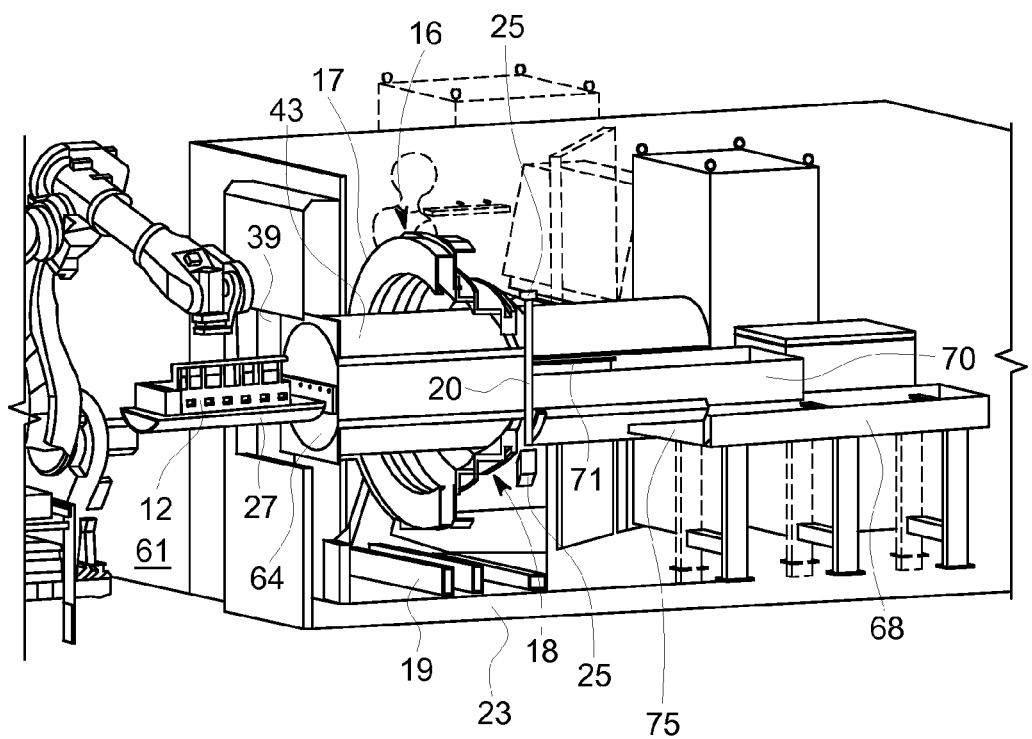
FIGS. 5, 6, and 7: show perspective views of an X-ray testing system at different points in time of the testing process.
Figure 6:
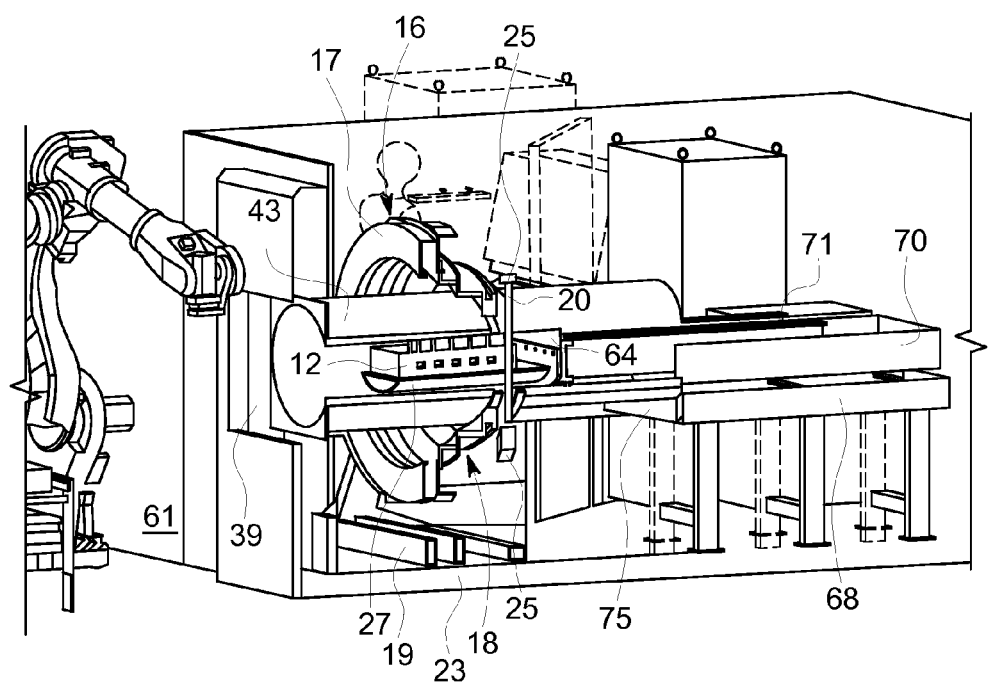
Figure 7:
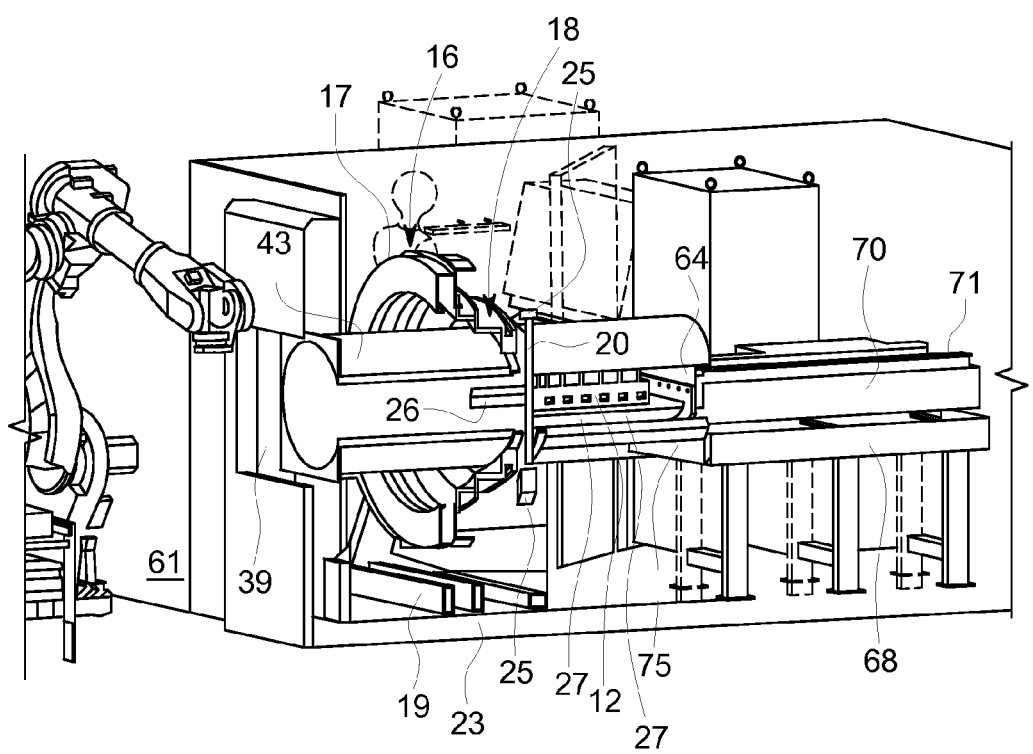

In particular, the X-ray detector 25 is a semiconductor detector and is in an embodiment digital with a direct conversion of the incident X-radiation into electric count pulses. In an embodiment, a line detector has a plurality of lines, and in an embodiment at least 16 parallel lines. The detector 25 in an embodiment has a sufficient length in order to acquire as large an angle range as possible of the X-radiation emitted by the tube 24. It is bent in the shape of a banana in an embodiment, so that the sensitive surface, as far as possible, has a substantially constant distance everywhere from the source point of the X-ray tube 24. In FIGS. 5 to 7, the banana-shaped detector 25 is cut off, so that here, only the ends of the detector 25 are visible. In order to obtain a sub-millimeter image resolution, the pixel size of the detector 25 is at most 1 mm, in an embodiment at most 0.7 mm.

During the X-ray testing of a component 12, the rotor 18 is continuously rotated about the central longitudinal axis of the ring unit 16 by means of rotational drives, which are not shown and which are attached to the support 17, with a plurality of complete 360° revolutions of the rotor 18 being carried out for each component 12. The electricity supply of the X-ray tube 24 co-rotating with the rotor 18 and the X-ray detector 25 is effected through a high voltage supply unit 79 by means of a slip ring assembly disposed between the rotor 18 and the support 17. The axis of rotation of the rotor 18, or the longitudinal axis of the ring unit 16, is in an embodiment oriented parallel to the translation direction of the component 12 through the testing/measuring device 11, and, in an embodiment, substantially horizontal.

For example, the system 10 is disposed on a conveying device 13, for example a roller or belt conveyor, for serially feeding and removing a plurality if substantially identical components 12 to be tested. The conveying device 13 is in an embodiment configured as a conveying line, i.e. as a translatory conveyor, and can be, for example, part of a production line.

The system 10 comprises, for example, a loading device 22, which in this case is configured as a robot. Other embodiments of the loading device 22 are possible. The loading device 22 serves for taking a component 12 to be tested from the conveyor 13, transfer it to the handling device 60 for testing (loading the testing device 11), taking the component 12 from the handling device 60 after testing (unloading the testing device 11) and placing it on the conveyor 13 for transport. The loading device 22 can be dispensable, particularly if the handling device 60 itself is configured for removing components 12 from, or placing them on, the conveying device 13. The handling device 60 can also be loaded and unloaded in a different way, for example manually.

In order to feed the components 12 into the protective enclosure 15 or to remove them from it, a loading opening 39 is provided in the protective enclosure 15 which can be sealed in a radiation-proof manner during X-ray testing, for example, by means of a slider, which is not shown, so that protection against radiation is ensured at all times.

Figure 3:
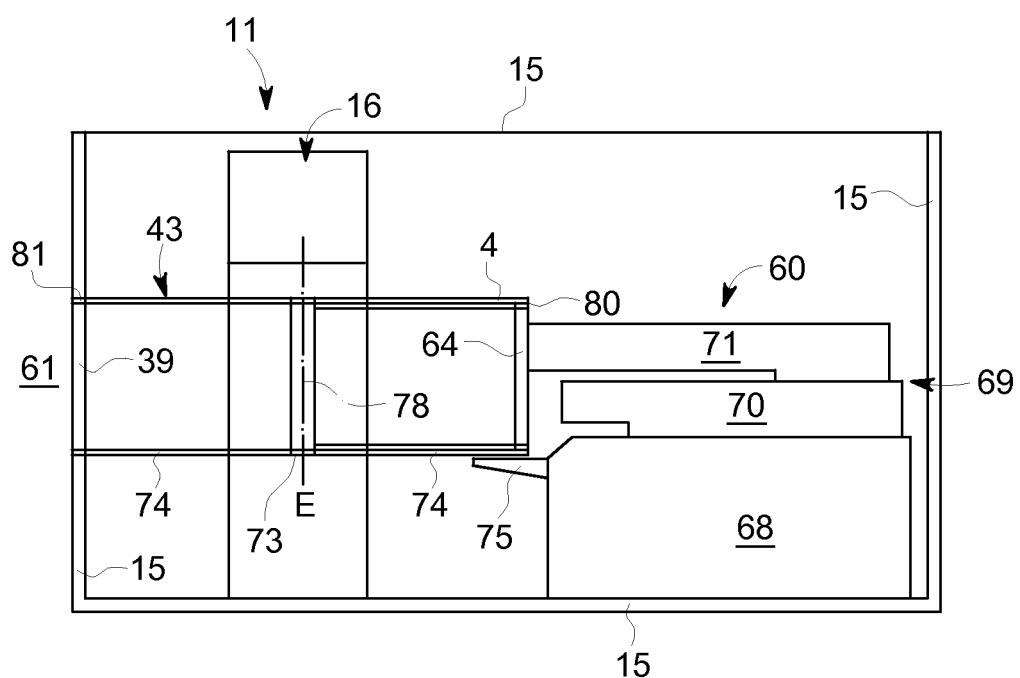
FIG. 3: shows a schematic cross-sectional view of an X-ray testing system in the region of the X-ray device.

A tube 43 is guided through the rotor 18, in particular in order to protect the testing device 11 and the ring unit 16 against dirt due to the introduction of the components 12, but also, for example, against damage due to incorrectly positioned components 12. The tube 43 defines a transport tunnel for the component 12 to be tested. The tube 43 in an embodiment extends from the loading opening 39 through the testing device 11, i.e. through the ring opening 26 of the ring unit 16, and by a minimum length over the testing device 11, which is defined by the plate 64 still being located inside the tube 43 in the position in which it is maximally retracted (see FIG. 3). For example, the tube 43 can protrude an equal distance over the testing device 11 in both directions, i.e. be disposed symmetrically relative to the testing plane E, as, for example, in FIG. 3. The testing plane E is in this case the plane extending perpendicularly to the rotor axis 18 and centrally through the X-radiation, i.e. in which the greatest X-ray intensity exists. The diameter of the tube 43 is expediently adapted to the inner diameter of the ring unit 16 in order to enable the testing of components 12 with as great a size as possible.

In an embodiment, the tube 43 is attached to the enclosure 15 at its front end, i.e. in the region of the loading opening 39. The load-side opening of the tube 43 thus in an embodiment forms the loading opening 39 in the enclosure 15. In an embodiment, the tube 43 is connected at its front end in an air-tight manner to the enclosure 15 at the edge defining the loading opening 39, particularly by means of an annular sealing member 81. At its rear end, the tube 43 can, for example, be retained on the base 68, for example by means of supports 75 attached to the base 68.

At least in the region in which it is exposed to X-radiation, the tube 43 is radiation-transparent. In an embodiment, the tube 43 is assembled from several sections, i.e. a central radiation-transparent section 73 in the region of the X-radiation and one or more, in particular two, sections 74 outside the region of the X-radiation, which, accordingly, do not have to be configured to be radiation transparent and which can therefore be formed from a less expensive material and more ruggedly. The tube sections 74, in particular, can be configured as half shells, for example, for better dismantling for maintenance purposes. The tube 43 is in an embodiment free from openings in the tube wall so that dirt particles, in particular, cannot enter the testing/measuring device 11 from the component 12.

In an embodiment, the handling device 60 serves for transporting a component 12 to be tested from a loading region 61, which is located outside the radiation protection enclosure 15 in front of the loading opening 39, into the testing region in the testing/measuring device 11, for handling the component 12 particularly during X-ray testing in the testing/measuring device 11, and for transporting it from the testing region back to the (un)loading region 61. In other words, both the loading of the handling device 60 with a component 12 to be tested and the unloading of the handling device 60 takes place in the same loading region 61, i.e. in an embodiment on the same side of the testing device 11 or the testing plane E.

The handling device 60 comprises a base 68 which is stationary on the floor, for example a base frame (see FIG. 3), and a displacing unit 69 that is axially displaceable on the base 68. Within the context of the present application, axial relates to the axis of the rotor 18. In an embodiment, the base 68 is mounted on the side of the testing device 11 or testing plane E opposite to the loading region 61, and in an embodiment in the radiation protection enclosure 15. The displacing unit 69 comprises at least one, in an embodiment a plurality of, in this case two, linear elements 70, 71 that can be displaced relative to each other. In particular, a first one of the linear elements 70 is axially displaceably mounted on the base 68, and the other one of the linear elements 71 is axially displaceably mounted on the first linear element 70. Therefore, the length of the displacing unit 60 can be changed in a telescoping fashion. The axial displaceability of the linear elements 70, 71 can be realized, in particular, by means of corresponding linear guides.

In an embodiment, the use of a plurality of linear elements 70, 71 can serve for separating the functions of the transport of the component 12 between the loading region 61 and the testing region from the displacement of the component 12 through the testing region during X-ray testing. In particular, the displacement of the linear element 71 relative to the linear element 70 can serve for the highly accurate, but comparatively slow, displacement of the component 12 through the testing region in the testing/measuring device 11 during X-ray testing. The displacement of the linear element 70 relative to the base 68 can, for example, serve for transporting a component 12 to be tested from the loading region 61 into the testing region 78 and for transporting it from the testing region 78 back into the (un)loading region 61. This transport does not have to take place at the same high speed and can therefore be carried out faster and using a less expensive drive.

In order to obtain a sub-millimeter resolution, the handling device 60 is in an embodiment adapted for conveying the components 12 through the testing region 78 at a substantially constant feed speed, i.e. with fluctuations in the feed speed of less than 10%, in an embodiment of less than 5%, in an embodiment of less than 1%. For this purpose, the linear guide between the linear elements 70, 71 in an embodiment comprises a drive that is controlled with the corresponding accuracy, and in an embodiment with a linear or servo motor, in order to achieve the required constancy in the feed speed. After the above statements, the drive 34 for the linear guide between the linear element 70 and the base 68 for transporting the component 12 before or after X-ray testing does not have to provide the same high constancy of speed and can therefore be configured to be less expensive.

A vertically oriented plate 64 is attached to the end face of the displacing unit 69 facing towards the testing device 11, in this case on the end face of the linear element 71. The shape of the plate 54 in an embodiment corresponds to the shape of the clear cross section of the ring unit 16 or of the tube 43. Therefore, in the present case of a tube 43 with a (circular) round cross section, the plate 64 is in an embodiment also circular. In an embodiment, the outer diameter of the plate 64 is adapted to the internal diameter of the ring unit 16 or of the tube 43. Therefore, the plate 64 in an embodiment fills the clear cross section of the rotor 18 or of the tube 43 substantially completely, i.e. in particular with the exception of a gap between the plate 54 and the tube 43, which is in an embodiment sealed in an air-tight manner by means of an annular sealing member 80.

The workpiece 12 is disposed or retained on the front of the plate 64, i.e. on the side facing towards the loading opening 39 and away from the base 68. As is apparent, for example, from FIG. 3, the entire clear cross section of the ring unit 16 or of the tube 43 is available, in principle, to the workpiece 12.

In an embodiment, an accommodating or retaining means for accommodating or retaining the workpiece 12 is provided on the front of the plate 64. This accommodating or retaining means can have a variety of configurations. In the exemplary embodiment of the Figures, this is, for example, a supporting member 27 that is attached to the plate 64 and has a level bearing surface 77 on which the component 12 rests. Though the supporting member 27 takes up a certain space, the supporting member 27 and its, in particular vertical, arrangement can be adapted to the component 12 to be tested, so that there is still considerably much more space available for the component 12 to be tested than in the prior art. The shape of the supporting member 27 is variable.

Alternatively, the accommodating or retaining means can, for example, be a clamping holder, gripping tool, device for hooking the component 12 into the plate 64, an accommodating container that is open at the top for inserting the component 12, a gripper with a plurality of fingers disposed at the same level, etc., all of which are provided on the front of the plate 64 or are or can be attached thereto. Many variations are possible in this case. A magnetic or electromagnetic accommodation, particularly for ferromagnetic components, for example in the form of a magnetic plate 64, is also conceivable. In an embodiment, the accommodating/retaining means can be adapted to the component 12 to be tested in each case. Therefore, the accommodating/retaining means in an embodiment is an adapter part. Moreover, the accommodating/retaining means can in an embodiment be detached from the plate 64 and replaced, for example, by another accommodating/retaining means. In an embodiment, the accommodating or retaining means is substantially transparent for X-radiation in order to affect the imaging of the component 12 as little as possible.

In an embodiment, the retaining part 27, or more generally the accommodating/retaining means, can be height-adjustable. A, for example, electrically driven height adjusting device 63 is provided for this purpose, which is in an embodiment attached to the plate 64, particularly to the rear thereof. In particular, the retaining part 27 is guided on the handling device 60 or on the plate 64 so as to be vertically displaceable. The height adjusting device 63 comprises, for example, one or more vertically disposed linear guides 65 and an electric drive 66 in addition to a corresponding gear unit. Because of the height-adjustability, the retaining part 27 can be adapted, for example, to components 12 with different dimensions so that a substantially central passage of the components 12 through the ring unit 16 can be ensured.

Moreover, the height adjustable retaining part 27 can optionally serve as a loading device 22. For example, the lowered retaining part 27 can be moved under a component 12 fed by the conveyor. By lifting the retaining part 27, the component is removed from the conveyor 13 and can then be tested. After testing, the retaining part 27 with the component 12 is moved over the conveyor 13 and lowered in order to place it on the conveyor and then transported away.

In general, the accommodating/retaining means can in an embodiment be displaceable and/or rotatable relative to the plate 64 about one or more axes. For example, the accommodating/retaining means can in an embodiment be displaceable along the axis of the rotor 18 or length-adjustable in a telescoping fashion, for example in order to obtain a sufficient reach for loading/unloading the conveyor 13. In that case, a separate loading device 22 can possibly be dispensable.

Figure 4:
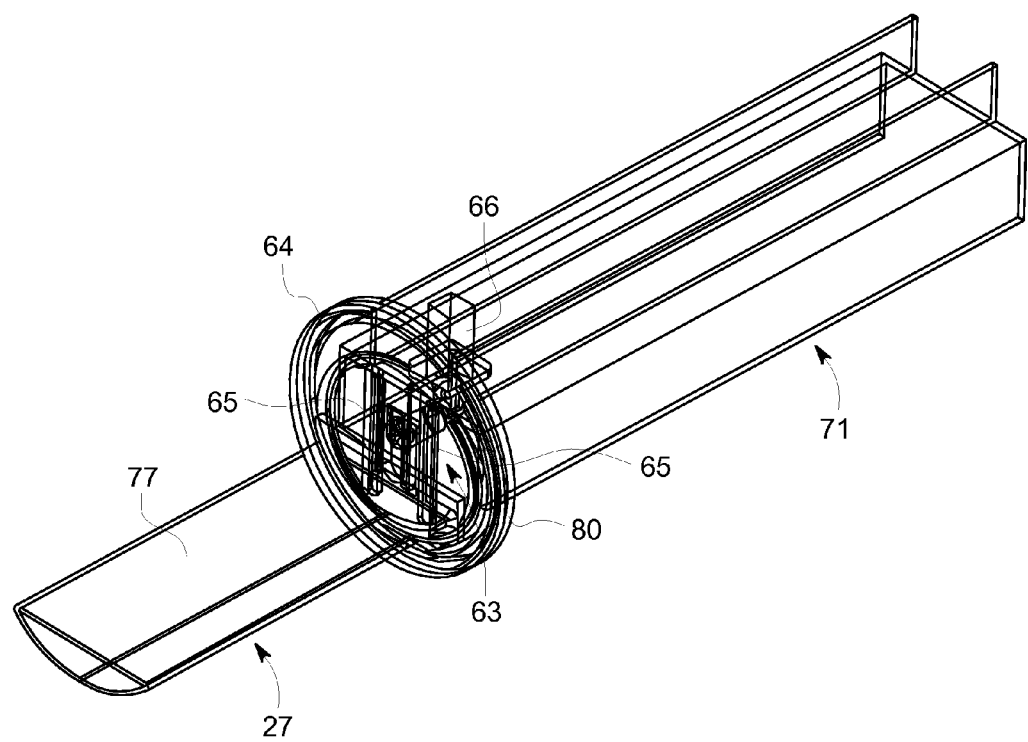
FIG. 4: shows a perspective view of a portion of a handling device for an X-ray device.

According to an embodiment of the invention, a maximum construction space is also available on the rear of the plate 64, i.e. on the side facing away from the loading opening 39 and towards the base 68. For this reason, the linear element 71, for example, can in an embodiment be configured in a very rugged manner. This is apparent, for example, from FIG. 4, where the linear element 71 in an embodiment has the shape of a double U profile with abutting basis legs. There is also a lot of space on the rear of the plate 64, for example, for the height adjusting device 63 and other functional devices, particularly if, in an embodiment, the linear element 71 is a profile.

Figure 2:
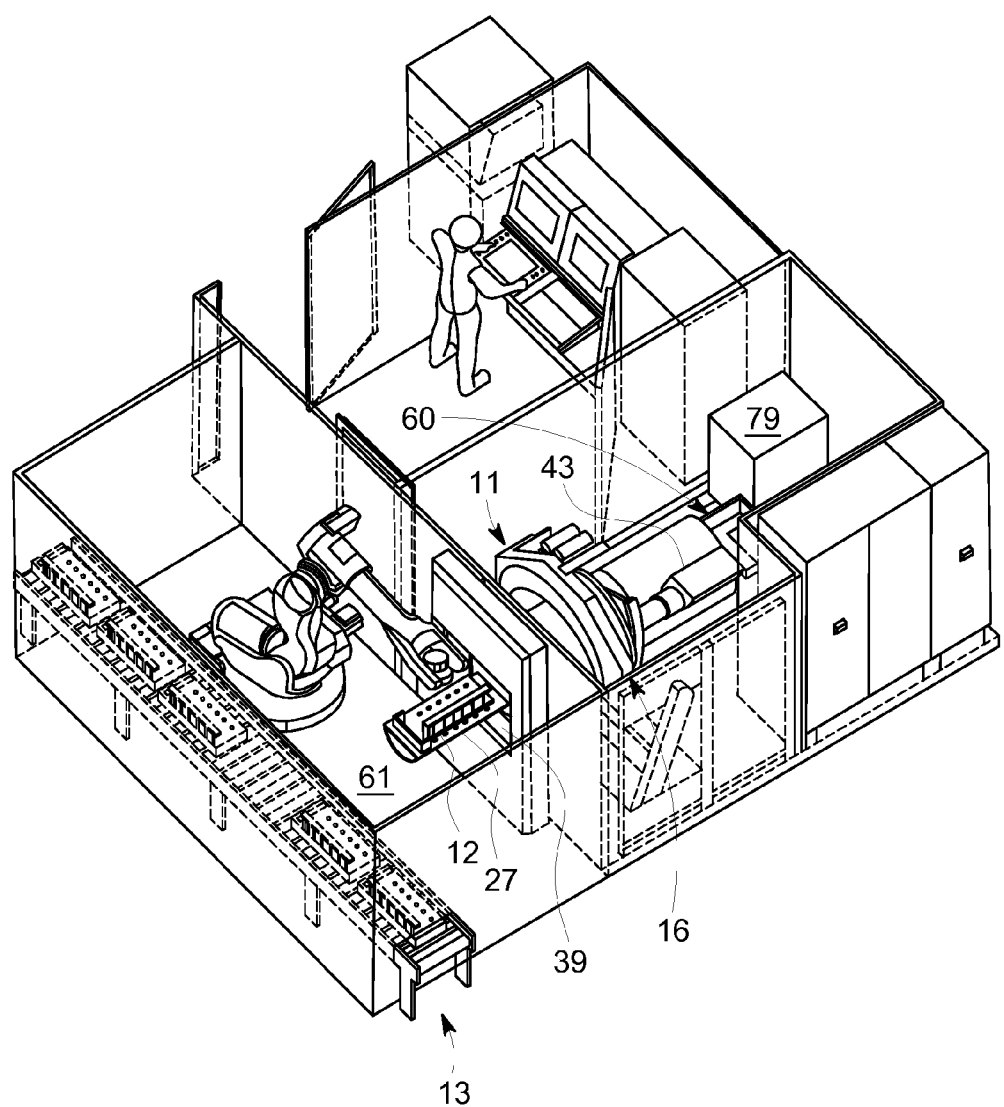
FIG. 2: shows a perspective view of an X-ray testing system.

The testing process proceeds as follows: For example, a component 12 to be tested is removed from the conveyor 13 by the loading device 22 and placed on the supporting member 27 of the handling device 60, or, more generally, transferred to the handling device 60. At this point in time, the handling device 60 is in the loading position, in which the displacing unit 69 is displaced towards the loading region 61 to the greatest extent and the region in front of the plate 64, in which the component is to be disposed (i.e. the accommodating/retaining means, in this case the supporting member 27), is located outside the protective enclosure 15. In particular, the plate 64 can end approximately flush with the front end of the tube 64 in this position, which is shown in FIGS. 1, 2 and 5.

Then, the plate 64 with the component 12 is pulled back by displacing the linear element 70, or the entire displacing unit 69, along the base 68 until the component 12 has almost reached the X-ray. Then, the displacement of the linear element 70 or of the displacing unit 69 is stopped and the transport of the component into the testing region 78 is completed.

Then, the plate 64 with the component 12 is pulled back further by displacing the linear element 71 along the linear element 70 with a highly constant, but possibly lower, speed and moved through the testing region 78, with the component 12 passing through the X-ray 20 and X-ray images being taken. A point in time during X-ray testing is shown in FIG. 6.

When the component 12 has left the X-ray beam 20 or the testing region 78, the displacement of the linear element 71 is stopped and the X-ray testing of the component is completed. This point in time is shown in FIG. 7. Here, the handling device 60 is pulled back the farthest.

Then, the plate 64 with the component 12 is pushed forward by displacing the linear element 70, or the entire displacing unit 69, along the base 68 with an increased transporting speed until the unloading state shown in the FIGS. 1, 2 and 5 has been reached. Because the plate 64 is in an embodiment sealed with respect to the tube 43 by means of an annular seal 80, the plate 64 in an embodiment pushes possible dirt out of the tube 43 after each testing process. For example, the tested component 12 is removed from the handling device 60 by the loading device 22 and placed on the conveyor 13 in order to be transported away, and the next component to be tested 12 is supplied.

Because of the translational displacement of the component 12 to be tested taking place during the test, which is carried out by the testing/measuring device 11 along the axis of rotation of the rotor 18, and the simultaneous continuous rotation of the X-ray system 24, 25 about the component 12 to be tested, the overall result is a helix-like movement of the X-ray system 24, 25 about the component 12 to be tested. A rotation of the component 12, in particular about a vertical axis, or a displacement about another axis, does not take place during the X-ray inspection. An additional manipulator for the component 12, such as a rotary table, is dispensable.

The control/evaluation unit 14 comprises a rapid CT reconstruction algorithm in order to convert the recorded X-ray data from the helical geometry into a volume or voxel representation. Moreover, the control/evaluation unit 14 comprises an algorithm for analyzing the volume image depending on the intended application. The evaluation of the X-ray signals by computer tomography makes it possible, in a manner known per se, to obtain information on the three-dimensional internal structure of the components, for example the exact position and shape of gas cavities in castings. In particular, this can be an automatic detection of internal material defects or anomalies such as gas cavities, porosities, as well as of inclusions of materials of higher density in a substantially homogeneous material of the component 12, which are determined by means of pre-defined testing parameters. Each component can optionally be graded "regular" or "irregular" and, optionally, be visually marked accordingly, or be rejected automatically. Finally, the control/evaluation unit 14 can comprise a communication unit for data exchange with an external unit, for example the central control unit of the production system. An automatic serial inspection of components 12 can be carried out, using the system 10, in a short time, which is compatible with the cycle times in a production line.

In addition or as an alternative to the helical scan mode, the control/evaluation unit 14 can also carry out axial scans and/or scans of only a part of the component 12, e.g. individual disks, or at certain positions.

As an alternative or addition to the detection of internal defects or anomalies of the component 12, the control/evaluation unit 14 can also be configured for determining the three-dimensional geometric dimensions of the components 12, i.e. the internal and external component structures, from the X-ray data. Optionally, a separate coordinate measuring device can in that case be omitted.

The correction for compensating the X-ray beam hardening effect, which is expediently carried out in the control/evaluation unit 14, is adapted to the inspection of typical materials, e.g. metals, alloys, composites, aluminum, iron etc.

The system 10 is delimited against devices for checking baggage, whose evaluation has to be adapted to an exceptional spectrum of certain baggage contents. In contrast, the device for inspecting a plurality of substantially identical components according to an embodiment of the invention can expediently be adapted, in a tailor-made manner, to the component to be tested, or to a mix of a limited number of component types. These devices are therefore made totally different, particularly with regard to the X-ray parameters and the evaluation algorithms. In an embodiment, the system is configured for obtaining a volume resolution in the X-ray image of less than or equal to 1 mm. Also because of this fact, an embodiment of the invention can be delimited against devices for checking baggage, which as a rule work with a resolution of some millimeters.

The device according to an embodiment of the invention can additionally or alternatively be used for material testing for measuring internal and external component structures (metrology). Optionally, a separate coordinate measuring device can in that case be omitted.

In order to prevent dust or moisture entering the protective enclosure 15, the latter is in an embodiment fully closed or sealed, with the exception of, for example, possible climate-control openings. In an embodiment, this is done by sealing the tube 43 with respect to the enclosure 15 in the region of the loading opening 39, particularly by means of an annular seal 81, as well as by sealing the plate 64 with respect to the tube 43, particularly also by means of an annular seal 80. Accordingly, the testing/measuring device 11 is disposed substantially encapsulated in the protective enclosure 15.

In order to dissipate the heat generated during the operation of the testing/measuring device 11 and to keep the interior of the protective enclosure 15 at a sufficiently low operating temperature even in very warm environments, such as in a foundry, a temperature-controlled, in particular electrically driven cooling unit, for example a air-conditioning system, is attached to the protective enclosure 15. In an embodiment, a device for overpressurizing the enclosure 15 is provided so that no dust or moisture is able to get into the protective enclosure 15 in the case of possible leaks, as well as through possible functional openings, such as an exhaust opening for the air-conditioning system. For example, this can be a compressed air connection which can be connected to an external compressed air source via a compressed air line. Alternatively, the overpressurization can also be carried out by means of the cooling unit.

The invention claimed is:

1. A system for the automated serial testing and/or measuring of a plurality of substantially identical components by X-radiation (X-ray), the system comprising:
 a testing device with a support;
 a rotor mounted so as to be continuously rotatable on the support
 an X-ray device disposed on the rotor;
 a protective enclosure surrounding the testing device;
 a handling device for handling a component during X-ray testing; and
 a control/evaluation unit configured for automatically controlling the system as well as evaluating the X-ray signals by computer tomography,
 wherein the handling device is configured for periodically reciprocating between a loading region and a testing region and comprises a vertically oriented end face element providing an accommodating and/or retaining mechanism on which the component can be disposed on the side of the end face element.

2. The system according to claim 1, wherein the handling device is mounted on the side of the testing device, or a testing plane opposite to the loading region.

3. The system according to claim 2, wherein the end face element is plate-shaped.

4. The system according to claim 2, wherein the accommodating/retaining mechanism comprises a supporting member for the component.

5. The system according to claim 2, wherein the accommodating/retaining mechanism comprises a clamping holder and/or a gripping tool for gripping the component and/or a gripper.

6. The system according to claim 2, wherein the accommodating/retaining mechanism is height-adjustable relative to the end face element.

7. The system according to claim 1, wherein the end face element is plate-shaped.

8. The system according to claim 1, wherein the accommodating/retaining mechanism comprises a supporting member for the component.

9. The system according to claim 8, wherein the accommodating/retaining mechanism comprises a clamping holder and/or a gripping tool for gripping the component and/or a gripper.

10. The system according to claim 9, wherein the accommodating/retaining mechanism is height-adjustable relative to the end face element.

11. The system according to claim 1, wherein the accommodating/retaining mechanism comprises a clamping holder and/or a gripping tool for gripping the component and/or a gripper.

12. The system according to claim 1, wherein the accommodating/retaining mechanism is height-adjustable relative to the end face element.

13. The system according to claim 1, further comprising a tube extending through the rotor wherein the end face element substantially extends over the entire cross section of the tube.

14. The system according to claim 1, wherein the end face element comprises on its outer circumference a sealing member.

15. The system according to claim 1, wherein the handling device is mounted on the side of the testing device, or a testing plane opposite to the loading region.

16. The system according to claim 1, wherein the handling device further comprises a first moveable section for conveying the component between the loading region and the testing region, and a second independently moveable section for the axial displacement of the component through the testing region during the test.

17. The system according to claim 16, wherein the length of the handling device can be changed in a telescoping fashion by the movable sections.

18. The system according to claim 1, wherein the control/evaluation unit is configured for the automatic detection of material defects such as gas cavities, porosities, as well as of inclusions of materials of higher density in a substantially homogeneous material of the component.

19. The system according to claim 1, wherein the end face element comprises on its outer circumference an angular sealing member.

20. A method for operating a system for the automated serial testing and/or measuring of a plurality of substantially identical components by X-radiation (X-ray), the method comprsing:
 transferring a component to be tested in a loading region to a handling device, which comprises a vertical oriented end face element providing a accommodating and/or retaining mechanism for the component;
 displacing the handling device in a linear manner in a feed direction from the loading region until the component has reached the testing region;
 displacing the handling device in a linear manner in order to move the component through the testing region for the purpose of X-ray testing; and
 displacing the handling device in a linear manner in a removal direction contrary to the feed direction from the testing region until the component has reached the loading region for unloading.

* * * * *